United States Patent
Boock et al.

(10) Patent No.: US 12,385,872 B2
(45) Date of Patent: Aug. 12, 2025

(54) WORKING WIRE FOR A BIOLOGICAL SENSOR

(71) Applicant: Allez Health Inc., Carlsbad, CA (US)

(72) Inventors: Robert James Boock, Carlsbad, CA (US); Khyati Mehta, Carlsbad, CA (US)

(73) Assignee: Allez Health Inc., Carlsbad, CA (US)

( * ) Notice: Subject to any disclaimer, the term of this patent is extended or adjusted under 35 U.S.C. 154(b) by 1077 days.

(21) Appl. No.: 17/302,415

(22) Filed: May 3, 2021

(65) Prior Publication Data

US 2021/0349048 A1   Nov. 11, 2021

Related U.S. Application Data

(60) Provisional application No. 63/021,212, filed on May 7, 2020.

(51) Int. Cl.
*G01N 27/327* (2006.01)
*A61B 5/1486* (2006.01)

(52) U.S. Cl.
CPC ...... *G01N 27/3271* (2013.01); *A61B 5/14865* (2013.01); *A61B 2562/125* (2013.01)

(58) Field of Classification Search
CPC .......... G01N 27/3271; A61B 2562/125; A61B 5/14865
USPC ....................................................... 428/357
See application file for complete search history.

(56) References Cited

U.S. PATENT DOCUMENTS

| | | |
|---|---|---|
| 2004/0138543 A1 | 7/2004 | Russell et al. |
| 2005/0004438 A1 | 1/2005 | Kenneth et al. |
| 2005/0084672 A1* | 4/2005 | O'Brien ................ C23C 14/562 |
| | | 428/364 |
| 2007/0129619 A1 | 6/2007 | Ward et al. |
| 2013/0056144 A1 | 3/2013 | Kotzan et al. |
| 2013/0197332 A1 | 8/2013 | Lucisano et al. |
| 2014/0343386 A1 | 11/2014 | Boock et al. |
| 2017/0055892 A1 | 3/2017 | Little et al. |
| 2019/0239778 A1 | 8/2019 | Srinivasan et al. |
| 2021/0106281 A1* | 4/2021 | Tran ...................... A61B 5/486 |

FOREIGN PATENT DOCUMENTS

| | | |
|---|---|---|
| TW | 201505971 A | 2/2015 |
| WO | 2010022252 A3 | 4/2010 |

OTHER PUBLICATIONS

International Search Report and Written Opinion dated Aug. 6, 2021 for PCT Patent Application No. PCT/IB2021/053693.
European Search Report dated Apr. 11, 2024 for European Patent Office Patent Application No. 21800742.5.
Official Letter and Search Report dated Dec. 4, 2024 for Taiwan Patent Application No. 110116254.
Office Action dated Feb. 28, 2025 for China Patent Application No. 202180033538.0.

* cited by examiner

*Primary Examiner* — Vincent Tatesure (74) *Attorney, Agent, or Firm* — MLO, a professional corp.

(57) ABSTRACT

A working wire for a biological sensor is disclosed. The working wire includes a substrate comprising cobalt-chromium (Co—Cr) alloy or Nitinol alloy, a platinum layer comprising platinum on the substrate, and a membrane layer comprising a biological membrane applied over the platinum layer.

11 Claims, 6 Drawing Sheets

WORKING WIRE FOR A BIOLOGICAL SENSOR

RELATED APPLICATIONS

This application claims priority to U.S. Provisional Patent Application No. 63/021,212 filed on May 7, 2020 and entitled "Working Electrode for a Continuous Biological Sensor," which is hereby incorporated by reference in full.

BACKGROUND OF THE INVENTION

Medical patients with diseases or conditions often require the measurement and reporting of biological conditions. For example, if a patient has diabetes, it is important that the patient have an accurate understanding of the level of glucose in their blood. Traditionally, diabetic patients monitor their glucose levels by sticking their finger with a small lance, allowing a drop of blood to form, and then dipping a test strip into the blood. The test strip with the blood sample is positioned in a handheld monitor that performs an analysis on the blood and visually reports the measured glucose level in the blood sample of the patient. Based upon the glucose level, the patient may need to lower or raise their glucose level. This is accomplished by making important decisions on what food to consume, or how much insulin to inject into their blood. It is advantageous for the patient to check their glucose levels many times throughout the day, but due to the pain and inconvenience, many patients fail to adequately monitor their glucose levels. As a result, the patient may eat improperly or inject either too much or too little insulin. Either way, the patient has a reduced quality of life and increased chance of permanent damage to their health and body. Diabetes is a devastating disease that if not properly controlled can lead to terrible physiological conditions such as kidney failure, skin ulcers, bleeding in the eyes, blindness, pain and sometimes, amputation of limbs.

Glucose monitoring is a complicated process and it is known that glucose levels in the blood can significantly increase or decrease quickly, due to several causes. Accordingly, a single glucose measurement provides only a snapshot of the instantaneous level of glucose in the patient's body. Such a single measurement provides little information about how the patient's use of glucose is changing over time, or how the patient reacts to specific dosages of insulin. The patient adhering to a strict schedule of blood strip testing may make incorrect decisions as to diet, exercise, and insulin injection since the blood strip test is only a snapshot of time. Of course, this is exacerbated when the patient is less consistent with performing strip testing. To give the patient a more complete understanding of their diabetic condition and to get a better therapeutic result, continuous glucose monitoring is used.

Monitoring the glucose level in the body is critical for diabetic patients. A continuous glucose monitoring device measures glucose in the patient's body from interstitial fluid sampled in an area just under the skin times a day. Continuous glucose monitoring devices typically involve a small housing in which the electronics are located and the housing is adhered to the patient's skin and worn for a period of time. A small needle within the continuous glucose monitoring device delivers the subcutaneous sensor which is often electrochemical. It will be understood that depending on the patient's needs, continuous glucose monitoring may be performed at different intervals. For example, some continuous glucose monitoring devices may be programmed to take multiple readings per minute, whereas in other cases, the continuous glucose monitoring device can be programmed to take readings every hour or so. It will be understood that a continuous glucose monitoring device may sense and report ratings at different intervals.

Electrochemical glucose sensors are commonly part of the continuous glucose monitoring device, and operate by using electrodes which typically detect an amperometric signal caused by oxidation of enzymes during conversion of glucose to gluconolactone in the patient's body. The amperometric signal can then be correlated to a glucose concentration. Two-electrode (also referred to as two-pole) designs use a working electrode and a reference electrode, where the reference electrode provides a reference against which the working electrode is biased. The reference electrodes essentially completes the electron flow in the electrochemical circuit. Three-electrode (or three-pole) designs have a working electrode, a reference electrode and a counter electrode. The counter electrode replenishes ionic loss at the reference electrode and is part of an ionic circuit.

Glucose readings taken by a sensor can be tracked and analyzed by a monitoring device, such as by scanning the sensor with a customized receiver or by transmitting signals to a smartphone or other device that has an associated software application. These are known as continuous glucose monitoring systems. Software features that have been included with continuous glucose monitoring systems include viewing glucose levels over time, indicating glucose trends, and alerting the patient of high and low glucose levels.

Unfortunately, the cost of using a continuous glucose monitoring system can be prohibitive for many patients that could benefit greatly from its use. As described generally above, a continuous glucose monitor has two main components. First, a housing encloses the electronics, processor, memory, wireless communication, and power source. The housing is typically reusable, and reusable over extended periods of time, such as months. The housing then connects or communicates to a disposable sensor that has been inserted subcutaneously into the patient. This sensor must be replaced, sometimes as often as every three days, or at least once every other week. Thus, the cost to purchase new disposable sensors represents a significant financial burden to patients and insurance companies. Because of this, a substantial number of patients that could benefit from continuous glucose monitoring are not able to use such systems and are forced to rely on the less reliable blood test strip— finger stick—monitoring. Accordingly, there is a significant need in the market for low-cost sensors for continuous glucose monitoring systems. By decreasing the cost of continuous monitoring, more patients could benefit from the increased quality of life and enhanced therapeutic effect of continuous monitoring.

Conventional continuous glucose monitoring systems typically use a working wire that uses a core of tantalum on which a thin layer of platinum is deposited. Tantalum is a relatively stiff material, so is able to be pressed into the skin without bending. Further, it is inexpensive as compared to platinum, which makes for an economical working wire. However, tantalum has the disadvantageous property of deforming permanently when placed under stress. For example, if a tantalum wire is wrapped onto a spool or roll, when unrolled, even short segments of the tantalum wire will retain some of the curvature of the roll. In another example, if the tantalum wire is bent while inserting into the skin, that bend will be permanent, and the working wire would need to be disposed.

SUMMARY

A working wire for a biological sensor is disclosed. The working wire includes a substrate comprising cobalt-chromium (Co—Cr) alloy, a platinum layer comprising platinum on the substrate, and a membrane layer comprising a biological membrane applied over the platinum layer.

A working wire for a biological sensor is disclosed. The working wire includes a substrate comprising Nitinol alloy, a platinum layer comprising platinum deposited over the substrate, and a membrane layer comprising a biological membrane applied over the platinum layer.

A method of manufacturing a working wire for a biological sensor is disclosed. The method includes receiving a substrate in a wound position. The substrate comprises a cobalt-chromium (Co—Cr) alloy or a Nitinol alloy. The substrate is unrolled from the wound position, and the substrate is allowed to transition from the wound position to a linear position. The substrate is separated into lengths suitable for the working wire. A platinum layer is provided on the substrate, and the platinum layer comprises platinum. A membrane layer is applied over the platinum layer, and the membrane layer comprises a biological membrane.

BRIEF DESCRIPTION OF THE DRAWINGS

Each of the aspects and embodiments of the invention described herein can be used alone or in combination with one another. The aspects and embodiments will now be described with reference to the attached drawings.

DETAILED DESCRIPTION

Biological sensors, such as electrochemical glucose sensors, are used for continuous glucose monitoring devices and systems. The sensor detects a concentration of an analyte in the patient, oftentimes by measuring the concentration or ion flow within the blood or other body fluids. It will be understood that a sensor may include multiple working wires, multiple reference electrodes, and counter electrodes which are constructed and arranged for the sensing. Generally, the working electrode which includes the working wire, is constructed to meet three basic requirements. First, it must be strong enough to withstand insertion under the patient's skin and then withstand the vibrations, shocks, and motions during use. Second, it needs to be flexible but straight and strong enough to follow a desired path into the skin, and to allow for some movement after insertion for patient comfort. Third, it needs to provide the electrical characteristics to support consistent and accurate sensing. Further, it is highly desirable that the working electrode and working wire can be readily and efficiently manufactured according to precise medical standards.

The embodiments disclosed herein are directed to a cost-effective biological sensor for use in a continuous glucose monitoring device and system. The embodiments provide a reduction in cost for the manufacture of the working wire of the working electrode, as well as provide superior straightness, flexibility, durability, and strength of the working wire of the working electrode. Further, the working wire of the working electrode has sufficient flexibility for patient comfort and movement, but is straight and stiff to enable accurate insertion along a desired insertion path without deformation. Although the embodiments are discussed primarily for the use in continuous glucose monitoring devices and systems, it will be understood that many other uses for biological sensing exist that would benefit from a reduced-cost sensor and working wire of the working electrode.

The embodiments disclosed herein enable the cost-effective manufacture of a working wire with superior mechanical strength and flexibility, which ultimately increases patient safety, comfort and the utility of the biological sensor. Further, the working wire of the working electrode is constructed of materials known to be safe in a human body. This also allows for the use of alternative geometries of sensor and different forms of sensor manufacture.

In some embodiments, the working wire is comprised of a Co—Cr alloy rather than tantalum. Tantalum is widely used in the industry for the working wire. Co—Cr alloy is known to be dense, ductile, very hard, easily fabricated, highly conductive of heat and electricity, and resistant to corrosion. However, Co—Cr alloy is more costly than tantalum, so it has not previously been used in this capacity. In other embodiments, the working wire is comprised of a "Nitinol" rather than tantalum. Nitinol alloy is an alloy comprised of nickel and titanium, and is also known to be dense, ductile, very hard, easily fabricated, highly conductive of heat and electricity, and resistant to corrosion. Nitinol alloy is most commonly available in an alloy having about 55% (by weight) nickel and about 60% nickel. Nitinol is electroactive in vitro, and cannot survive uncoated in the human body. If placed under the skin, and a current is applied, Nitinol will erode and structurally deteriorate the wire. Nitinol may be coated to avoid the electroactive erosion, but providing such a coating adds cost and complexity to manufacturing, so has not been previously used.

In this disclosure, Co—Cr alloy shall be used to mean an alloy of only cobalt (Co) and chromium (Cr). Nitinol alloy shall be used to mean an alloy of only nickel and titanium. In some embodiments the Co—Cr alloy or the Nitinol alloy can further include other additives or elements. For example, the Co—Cr alloy may be further alloyed with nickel, molybdenum, or magnesium, depending on application specific requirements. It will be appreciated that other additives or elements may be added. In one particular application, the Co—Cr alloy or Nitinol alloy wire may be made in a straight, linear position, and then treated, for example by annealing. The Co—Cr alloy or Nitinol alloy wire can be wound onto spools or rolls for storage, distribution, and use in automated manufacturing machines. Upon unwinding, the Co—Cr alloy or Nitinol alloy wire may automatically return to its original straight shape, or in some embodiments, a process may be applied to the Co—Cr alloy or Nitinol alloy wire to aid in transforming the wire from a wound position to its original shape, or a linear position. For example, the Co—Cr alloy or Nitinol alloy wire may be heated, cooled, have airflow applied, or another process to enable the Co—Cr alloy or Nitinol alloy wire to return to its original straight shape. Subsequently, the Co—Cr alloy or Nitinol alloy wire may be separated into suitable lengths as needed for the working wire, and will exhibit the straightness required for utilizing it as a working wire for a biological sensor, despite having been previously rolled onto a spool.

The Co—Cr alloy or Nitinol alloy substrate, i.e., wire used as a core for a biological sensor, is sufficiently strong to support insertion into human body, while having the needed flexibility for insertion and patient comfort. The Co—Cr alloy or Nitinol alloy substrate may include a platinum layer that has been formed using a drawn filled tube (DFT) process, deposition or electroplating. In the DFT process, the metal core is comprised of the Co—Cr alloy or Nitinol alloy, and the outer tube is comprised of platinum. The Co—Cr alloy as the core and platinum as the tube, or the Nitinol alloy as the core and the platinum as the tube, are drawn until the desired diameter of wire is achieved. In this way, the elongated wire is formed with a Co—Cr alloy or Nitinol alloy core and a platinum coating. Alternatively, if a thinner platinum layer is desired, the Co—Cr alloy or Nitinol alloy may be formed into the elongated wire, and then coated with the platinum using a deposition or electroplating process. Generally, the platinum layer has a thickness in a range from 20 to 100 microns, but typically is in the range of 25-40 microns.

In embodiments when the substrate is comprised of Nitinol alloy, a protective layer may be applied between the Nitinol alloy and platinum, since Nitinol alloy is electroactive. The protective layer may be comprised of nickel or gold. To complete the biological sensor, one or more membrane layers may be applied or deposited over the platinum. A total thickness of the working wire, including the Co—Cr alloy or Nitinol alloy, the protective layer if necessary, the platinum layer and the membrane layer, may be in the range of 0.0025 inches to 0.005 inches. In some embodiments, the thickness of the working wire may be 0.0033 inches.

In some applications, further strength and flexibility may be obtained by the Co—Cr alloy or Nitinol alloy substrate having a titanium core. Generally, the titanium core will have the same cross-sectional shape as the alloy substrate, but of a smaller diameter. It will be understood that the titanium may have other relationships to the alloy substrate shape to support specific applications, according to the availability of materials. Titanium is a transition metal known to be lightweight with low density and having exceptional strength. It is also highly resistant to corrosion. Titanium may be used in its elemental form, but is often used in alloy form with aluminum, vanadium, molybdenum or iron. It will be understood that titanium alloys can be used to support specific applications.

In one specific example, a titanium alloy commonly referred to as a Ti-6Al-4V, is used as the core in the Co—Cr alloy or Nitinol alloy substrate. Ti-6Al-4V has a particularly high strength to weight ratio, and superior corrosion resistance. Further, it has been widely used for implants and prostheses for humans, firmly establishing a safety record. Embodiments include using titanium-vanadium alloys as the core in the Co—Cr alloy or Nitinol alloy substrate.

The Co—Cr alloy and Nitinol alloys may exhibit a shape memory effect, whereby the alloy "remembers" its original shape, such as a straight, linear position, and can be temporarily deformed, but then returns to its original shape when the deforming load is released. This means that a straight Co—Cr alloy or Nitinol alloy wire can be made and processed and then wound onto rolls for easy and economical shipment. Later, the Co—Cr alloy or Nitinol alloy wire can be unwound, and the wire will return to its original straight condition. In some embodiments, the Co—Cr alloy or Nitinol alloy wire will naturally return to its original condition, and in other embodiments a process may be applied to the wire in order to return to its original condition. For example, applying heat, cold, airflow or other temperature cycling may be implemented.

The Co—Cr alloy or Nitinol alloy wire may be separated such as by cutting to the needed length for the working wire. In this way, a working wire may be constructed that is straight, durable, strong, flexible and has exceptional electrical and sensitivity characteristics. As the working wire has these superior characteristics, the working wire of the working electrode may be confidently and safely inserted into the patient, increase patient comfort and increase the effective positioning of the resulting biological sensor.

Figure 1A:
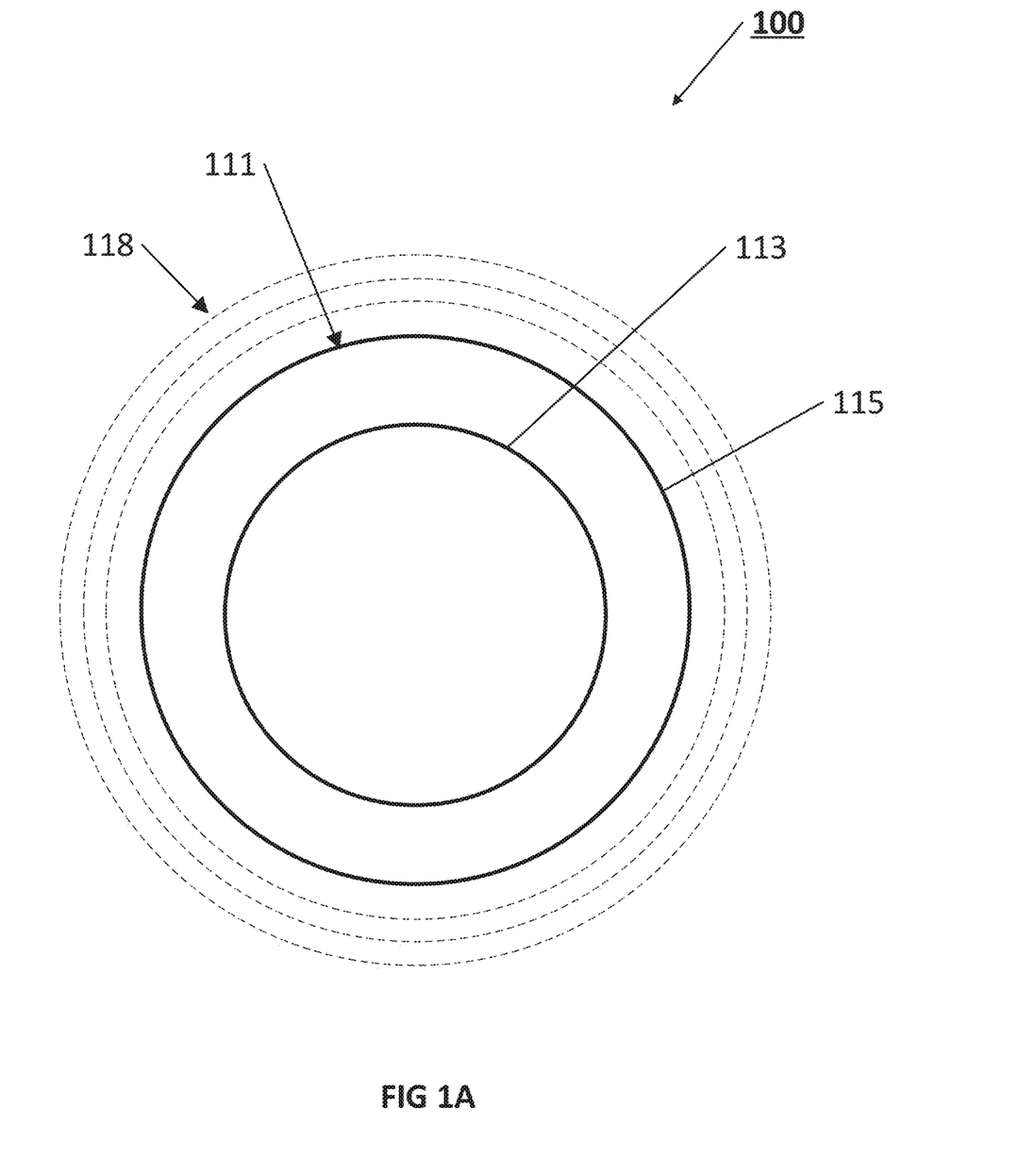
FIGS. 1A, 1B, 2A and 2B are cross-sectional views of working wires for a biological sensor, in accordance with some embodiments.

FIG. 1A is a cross-sectional view of a working wire for a biological sensor, in accordance with some embodiments. As shown, the working wire 100 is an elongated wire having a circular cross-section. It will be understood that the working wire 100 may have other cross-section shapes, such as square, rectangular, triangular, or other geometric shapes. It will further be understood that the working wire 100 may take other forms, such as a plate or ribbon. The working wire 100 has a substrate 111 comprised of cobalt-chromium (Co—Cr) alloy and platinum. Co—Cr alloy is in the form of a substrate or wire such as a Co—Cr alloy wire 113. Co—Cr alloy is a cost-effective alloy known to be dense, ductile, very hard, easily fabricated, highly conductive of heat and electricity, and renowned for its resistance to corrosion. Accordingly, the Co—Cr alloy provides an excellent substrate for the working wire 100. A platinum layer 115 comprising platinum is a thin coating of platinum deposited or applied on the Co—Cr alloy wire 113. The applying may include using a Drawn Filled Tube (DFT) process, or depositing the platinum layer using chemical deposition or electroplating.

The DFT process allows the matching of dissimilar materials to provide a variety of properties in a single wire system. Most commonly, the inner core of the composite provides strength while the outer sheath material is used to provide conductivity. DFT involves inserting a metal core into an outer tube and then drawing and annealing the combination. The DFT process was developed to combine the strength and biocompatibility of implant alloys with the properties of other materials. It will be understood that other processes may be substituted for applying the platinum layer 115 to the Co—Cr alloy wire 113. The platinum layer 115 may have a thickness in a range from 20 to 100 microns, although it will be appreciated that other thicknesses may be used.

The working wire 100 includes a membrane layer 118 disposed over the platinum layer 115 of the substrate 111. In this example, the membrane layer 118 is illustrated as three layers, and it will be understood that the membrane layer 118 may have more or fewer layers. The membrane layer 118 is a biological membrane, and as such, the application of biological membranes is well-known in the art and will not be discussed in great detail. Briefly, the biological membranes are polyurethane based and provide for enzyme stability in implant as well as diffusion control for a known metabolite (i.e., glucose).

For use as a working wire 100, a distal end of the working wire 100 may be sharpened or lubricated for easier insertion into the patient. For example, the distal end of the working wire 100, or a tip of the working wire 100, may be shaped to a pointed formation. In one example, the Co—Cr alloy wire 113 is selected to have a diameter and strength such that it can pierce the skin of the patient and the working wire 100 can be inserted without the use of a disposable inserter needle. This not only reduces cost but simplifies the insertion process for the patient. Due to its desirable flexibility, strength, and straightness, the working wire 100 can be confidently inserted along a desired insertion path yet accommodate patient comfort and movement. Further, the Co—Cr alloy wire 113 may be successfully straightened after being in a wound position, such as on a spool, thereby avoiding buckling or bending as it is inserted into the skin of the patient. This improved straightness also enables enhanced functionality and efficiency in manufacturing, for example, to enable precise dip coating of the working wire.

The working wire 100 may be formed into a thickness to support application specific needs, and according to the physical properties of the particular Co—Cr alloy used. The working wire 100 may have a thickness, or total diameter, in a range from 0.0025 inches to 0.005 inches which has been proven to be effective. That is, the working wire and its associated reference wire are sized to be insertable using a standard 25 or 26 gauge needle, and therefore must fit into the needle body. It will be appreciated that other wire diameters may be used to support other needle gauges. In some embodiments, the working wire 100 may have a thickness of 0.0033 inches. It will be appreciated that other thicknesses may be used.

Figure 1B:
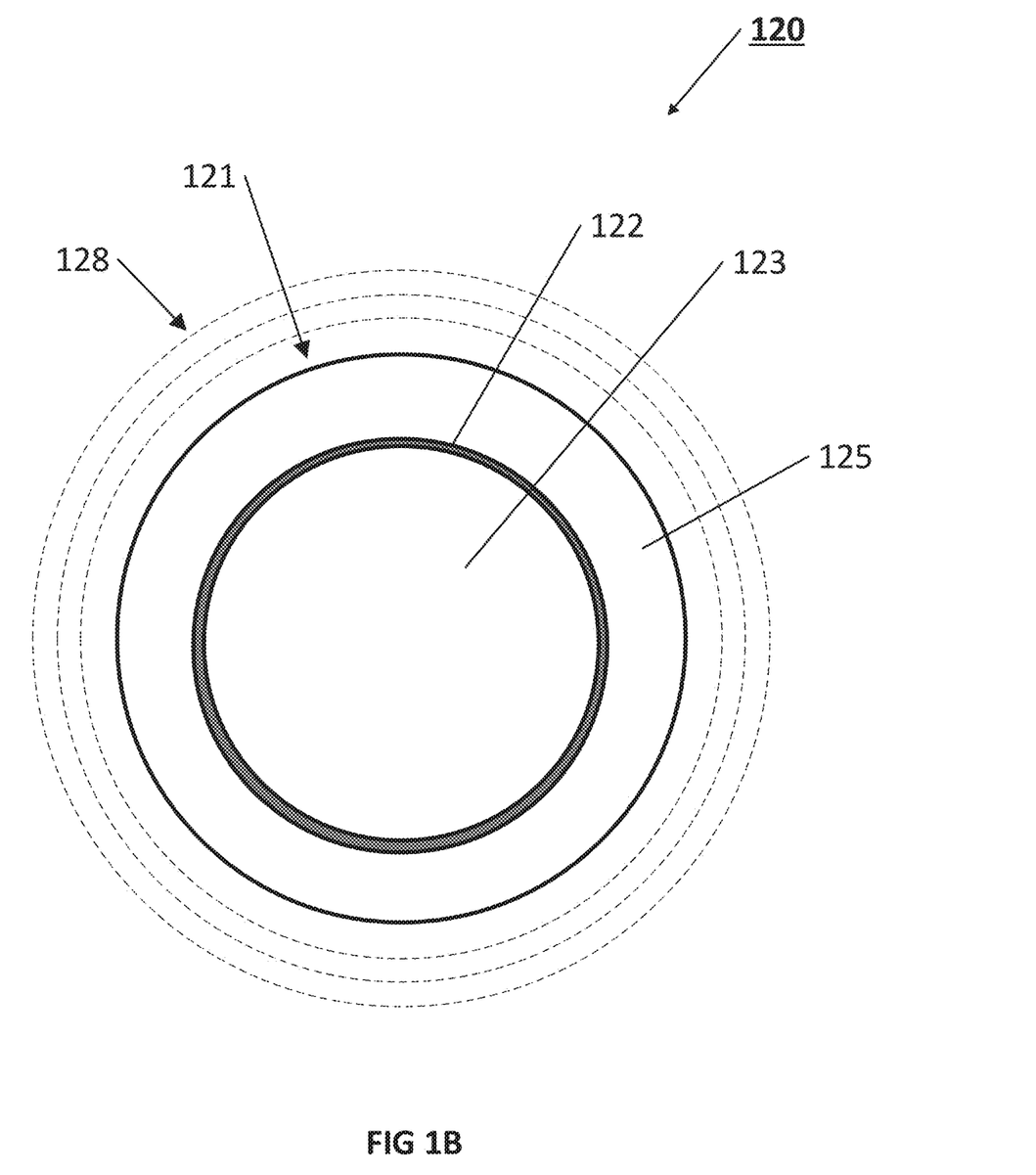

FIG. 1B is a cross-sectional view of a working wire for a biological sensor, in accordance with some embodiments. A working wire 120 is illustrated in cross-sectional form. In this example, the working wire 120 is an elongated wire having a circular cross-section. It will be understood that other cross-sections may be used, such as square, rectangular, triangular, or other geometric shapes. It will further be understood that the working wire 120 may take other forms, such as a plate or ribbon.

The working wire 120 has a substrate 121 comprised of Nitinol alloy, platinum and a protective layer. The Nitinol alloy is in the form of a substrate or wire such as a Nitinol alloy wire 123. Nitinol alloy is an alloy comprised of nickel and titanium, and typically, the two elements are present in roughly equal atomic percentages. In some embodiments, the Nitinol alloy is comprised of 55% nickel (by weight) or 60% nickel. Nitinol alloy is a cost-effective alloy known to be dense, ductile, very hard, easily fabricated, and highly conductive of heat and electricity. The alloy is renowned for its resistance to corrosion. Accordingly, Nitinol alloy provides an excellent substrate for the working wire 120.

As Nitinol alloy is electroactive, a protective layer 122 is applied on the Nitinol alloy wire 123 of the substrate 121. The protective layer 122 may be, for example, a thin layer of nickel or gold having a thickness in a range from 3 to 55 microns. In some embodiments the layer of nickel or gold has a thickness of 3-5 microns. It will be appreciated that other materials may be used. The Nitinol alloy wire 123 may then have a platinum layer 125 comprising platinum deposited or applied over the protective layer 122. This may be a thin coating of platinum and may be applied using the Drawn Filled Tube (DFT) process, or depositing the platinum layer using chemical deposition or electroplating. For example, the protective layer 122 may be located between the Nitinol alloy wire 123 and the platinum layer 125. It will be understood that other processes may be substituted for applying the platinum layer 125 to the Nitinol alloy wire 123. The platinum layer 125 may have a thickness in a range from 20 to 100 microns, although it will be appreciated that other thicknesses may be used.

The working wire 120 includes a membrane layer 128 disposed over the platinum layer 125 of the substrate 121. In this example, the membrane layer 128 is illustrated as three layers, and it will be understood that the membrane layer 128 may have more or fewer layers. The membrane layer 128 is a biological membrane as disclosed with reference to FIG. 1A.

For use as a working wire 120, a distal end of the working wire 120 may be sharpened or lubricated for easier insertion into the patient. For example, the distal end of the working wire 120, or a tip of the working wire 120, may be shaped to a pointed formation. In one example, the Nitinol alloy wire 123 is selected to have a diameter and strength such that it can pierce the skin of the patient and the working wire 120 can be inserted without the use of a disposable inserter needle. This not only reduces cost but simplifies the insertion process for the patient. Due to its desirable flexibility, strength, and straightness, the working wire 120 can be confidently inserted along a desired insertion path yet accommodate patient comfort and movement. Further, the Nitinol alloy wire 123 may be successfully straightened after being in a wound position, such as on a spool, thereby avoiding buckling or bending as it is inserted into the skin of the patient. This improved straightness also enables enhanced functionality and efficiency in manufacturing, for example, to enable precise dip coating of the working wire.

The working wire 120 may be formed into a thickness to support application specific needs, and according to the physical properties of the particular Nitinol alloy used. The working wire 120 may have a thickness in a range from 0.0025 inches to 0.005 inches which has been proven to be effective. That is, the working wire and its associated reference wire are sized to be insertable using a standard 25 or 26 gauge needle, and therefore must fit into the needle body. It will be appreciated that other wire diameters may be used to support other needle gauges. In some embodiments, the working wire 120 may have a thickness of 0.0033 inches. It will be appreciated that other thicknesses may be used.

Figure 2A:
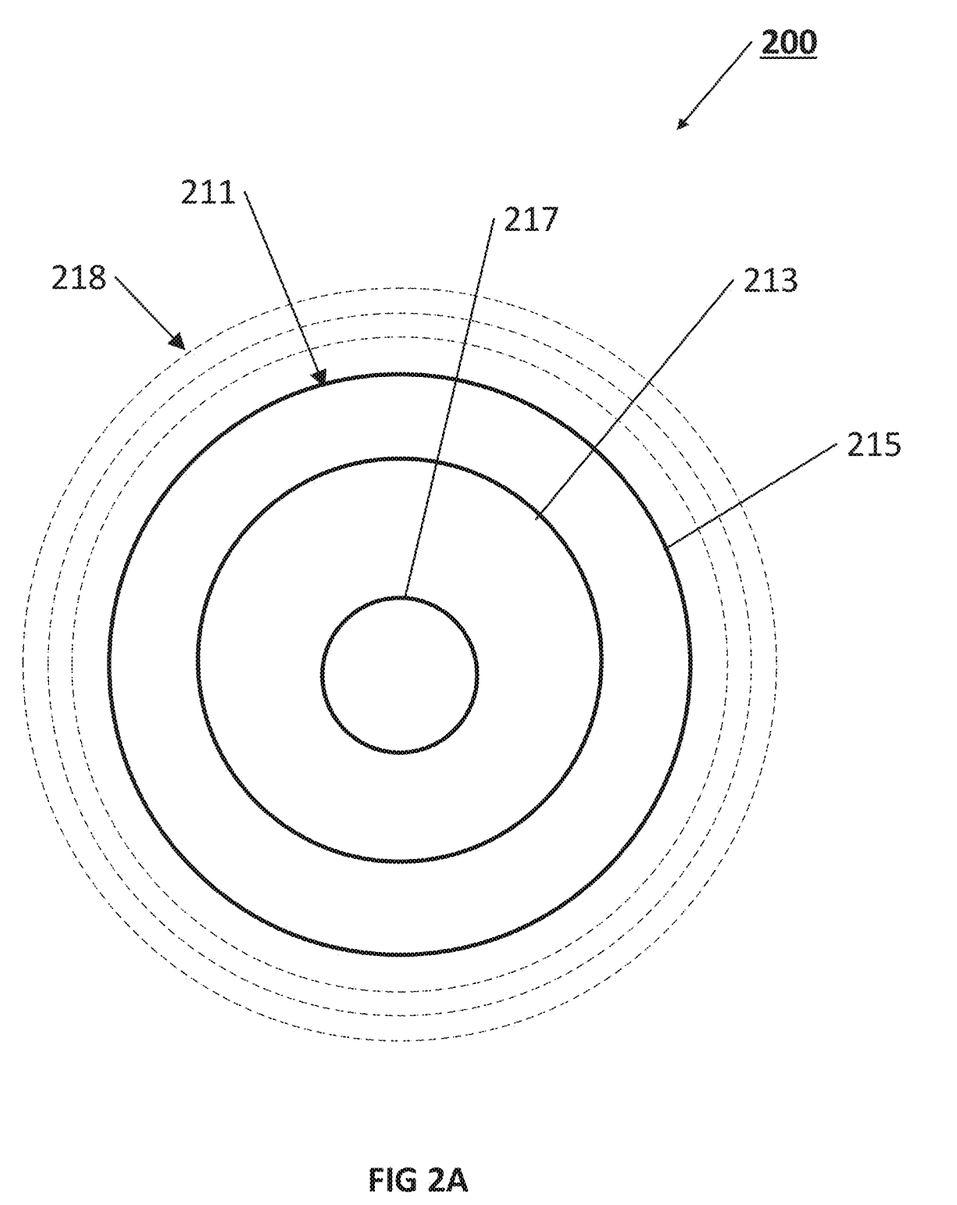

FIG. 2A is a cross-sectional view of a working wire 200 for a biological sensor, in accordance with some embodiments. As shown, the working wire 200 is an elongated wire having a circular cross-section. It will be understood that the working wire 200 may have other cross-section shapes such as square, rectangular, triangular, or other geometric shapes. It will further be understood that the working wire 200 may take other forms, such as a plate or ribbon.

The working wire 200 has a substrate 211 comprised of Co—Cr alloy, titanium and platinum. In the example of FIG. 2A, the substrate 211 includes a Co—Cr alloy wire 213 having a core 217 being a different material than the Co—Cr alloy wire. The core 217 may be comprised of titanium which forms an elongated Co—Cr alloy/core wire 213. Co—Cr alloy and titanium are cost-effective materials known to be strong, easily fabricated, and resistant to corrosion. Accordingly, the Co—Cr alloy/core wire 213 provides an excellent substrate 211 for the working wire 200. A platinum layer 215 comprising platinum may be deposited or applied to the Co—Cr alloy/core wire 213 to form a thin coating of platinum. This may be accomplished, for example, using chemical deposition or an electroplating process. It will be understood that other processes may be substituted for applying the platinum layer 215 to the Co—Cr alloy/core wire 213.

The working wire 200 includes a membrane layer 218 disposed over the platinum layer 215. Similar to FIGS. 1A and 1B, the membrane layer 218 is illustrated as three layers, and it will be understood that the membrane layer 218 may have more or fewer layers. As described herein, the membrane layer 218 is a biological membrane as disclosed with reference to FIGS. 1A and 1B.

As shown in FIG. 2A, the core 217 has the same cross-section shape as the substrate 211, but with a smaller diameter from 25 to 100 microns. It will be understood that the core 217 may have other shapes, depending upon material availability and specific process needs. In some embodiments, the cross-section shape of the core 217 may be different than cross-section shape of the substrate 211. In one specific example, the core 217 is comprised of Ti-6Al-4V, which sometimes is referred to as TC4, Ti64, or ASTM Grade 5, and is a titanium alloy. Ti-6Al-4V is known to have superior weight to strength ratios and corrosion resistance, as well as being fully tested and approved for use within the human body. It will be understood that other titanium alloys may be used. Titanium may be used in its elemental form, but may also be used in alloy form with aluminum, vanadium, molybdenum or iron. It will be understood that many titanium alloys can be used to support specific applications. For example, titanium alloys using vanadium have also shown desirable weight to strength ratios and corrosion resistance. The use of a titanium core or a titanium alloy core advantageously improves the flexibility to accommodate patient comfort and movement, and provides additional straightness to enable the accurate positioning of the working wire during the insertion process. In this way, the working wire can be confidently and comfortably positioned in the patient.

Figure 2B:
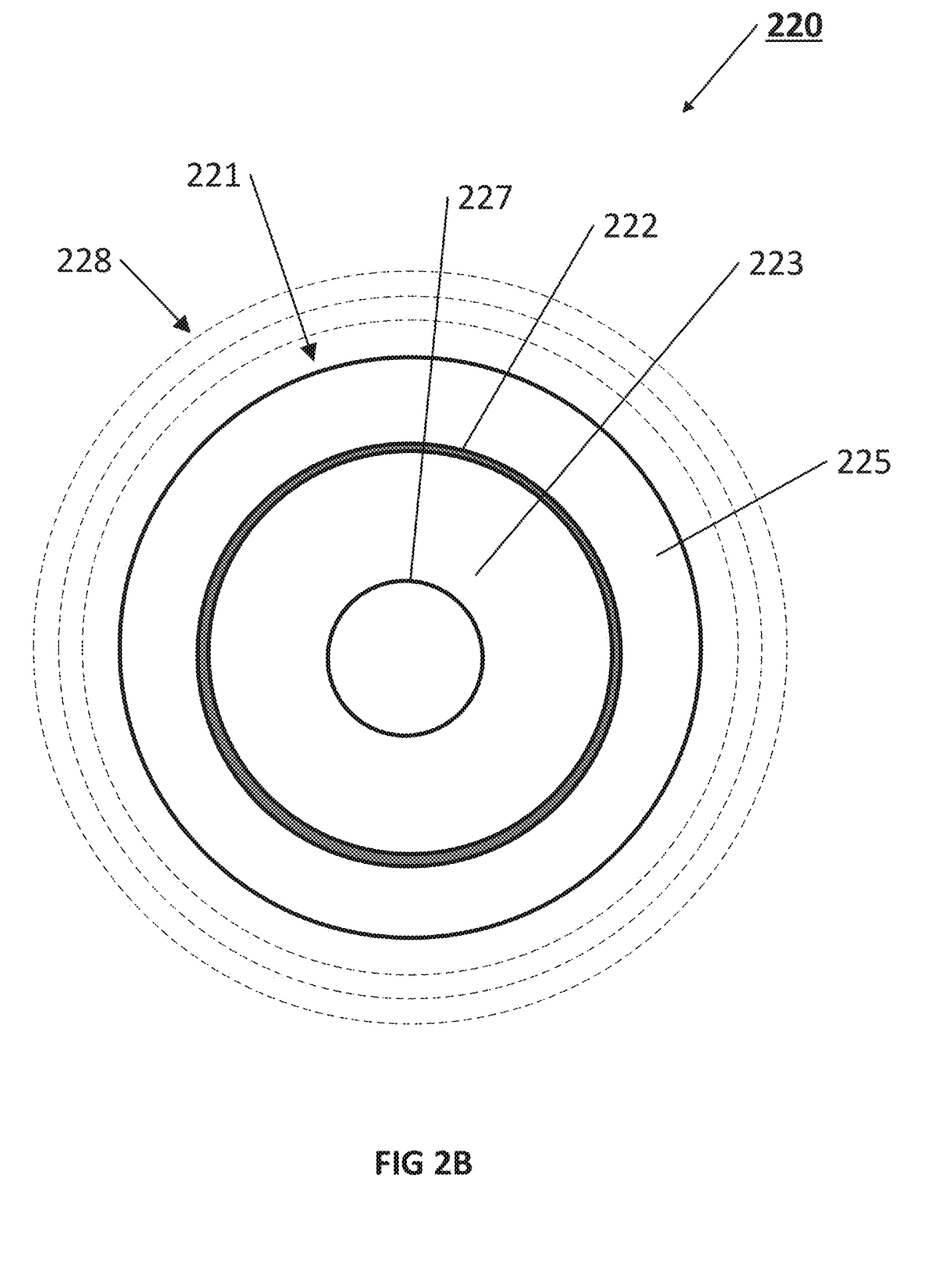

FIG. 2B is a cross-sectional view of a working wire 220 for a biological sensor, in accordance with some embodiments. As shown, the working wire 220 is an elongated wire having a circular cross-section. It will be understood that the working wire 220 may have other cross-section shapes such as square, rectangular, triangular, or other geometric shapes. It will further be understood that the working wire 200 may take other forms, such as a plate or ribbon.

The working wire 220 has a substrate 221 comprised of Nitinol alloy, titanium, platinum and a protective layer. In the example of FIG. 2B, the substrate 221 includes a Nitinol alloy wire having a core 227 being a different material than the wire. The core 227 may be comprised of titanium which forms an elongated Nitinol alloy/core wire 223. Nitinol alloy and titanium are cost-effective materials known to be strong, easily fabricated, and resistant to corrosion. Accordingly, the Nitinol alloy/core wire 223 provides an excellent substrate 221 for the working wire 220. A thin coating of platinum may be deposited or applied to the Nitinol alloy/core wire 223 to form a platinum layer 225. This may be accomplished, for example, using an electroplating process. It will be understood that other processes may be substituted for applying the platinum layer 225 to the Nitinol alloy/core wire 223.

The working wire 220 includes a membrane layer 228 disposed over the platinum layer 225. Similar to FIGS. 1A and 1B, the membrane layer 228 is illustrated as three optional layers, and it will be understood that the membrane layer 228 may have more or fewer layers. As described herein, the membrane layer 228 is a biological membrane.

As shown in FIG. 2B, the core 227 has the same cross-section shape as the substrate 221, but with a smaller diameter. It will be understood that the core 227 may have other shapes, depending upon material availability and specific process needs. In some embodiments, the cross-section shape of the core 227 may be different than cross-section shape of the substrate 221. In one specific example, the core 227 is comprised of Ti-6Al-4V, which sometimes is referred to as TC4, Ti64, or ASTM Grade 5, and is a titanium alloy. Ti-6Al-4V is known to have superior weight to strength ratios and corrosion resistance, as well as being fully tested and approved for use within the human body. It will be understood that other titanium alloys may be used. Titanium may be used in its elemental form, but may be used in alloy form with aluminum, vanadium, molybdenum or iron. It will be understood that many titanium alloys can be used to support specific applications. For example, titanium alloys using vanadium have also shown desirable weight to strength ratios and corrosion resistance. The use of a titanium core or a titanium alloy core advantageously improves the flexibility to accommodate patient comfort and movement, and provides additional straightness to enable the accurate positioning of the working wire during the insertion process. In this way, the working wire can be confidently and comfortably positioned in the patient.

Figure 3:
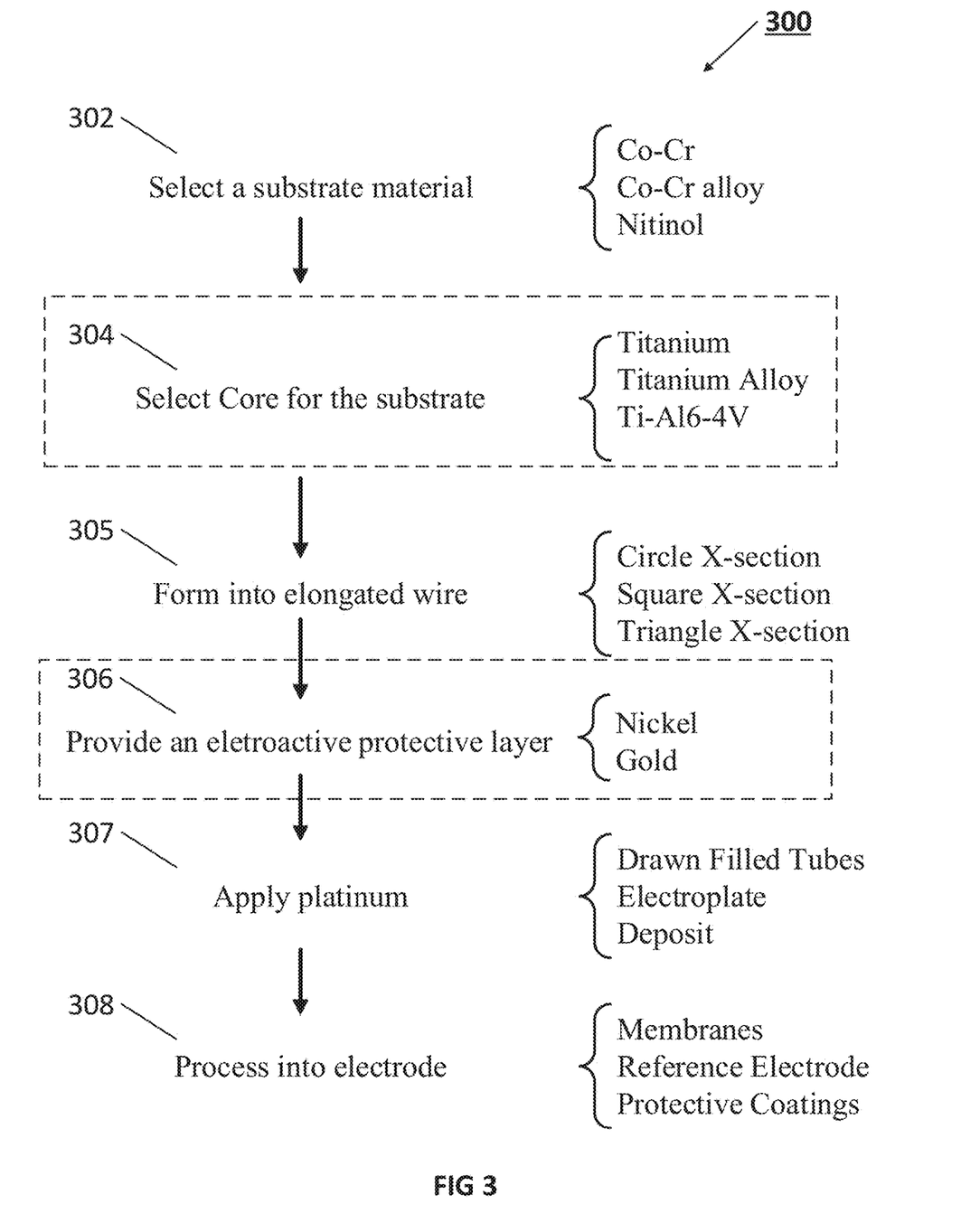
FIGS. 3 and 4 are flowcharts of methods for manufacturing a working wire for a biological sensor, in accordance with some embodiments.

FIG. 3 is a flowchart of a method 300 for manufacturing a working wire for a biological sensor, in accordance with some embodiments. At block 302, an alloy substrate material is selected. For example, the alloy substrate material may be elemental Co—Cr without additives, or a Co—Cr alloy and may further include nickel, molybdenum or manganese. In another embodiment, the alloy substrate may be Nitinol alloy. It will be understood that other additives or elements may be used as required for specific applications.

In some cases, the alloy substrate selected in block 302 may have a core made of a different material than the substrate material thereby having an alloy/core as shown in FIGS. 2A and 2B. Optionally, as indicated by the broken line block, at block 304, the core may be comprised of titanium, a titanium alloy, or in a specific example, the core may be Ti-6Al-4V. By using the titanium or titanium-based core with the alloy substrate, the working wire may have superior strength characteristics for a lower overall weight, and exhibit the ability to maintain a straight insertion path when inserted in the patient.

At block 305, the alloy or the alloy/core, may then be formed into an elongated wire. In some embodiments, it may be formed into other shapes such as ribbons or plates. The alloy or alloy/core elongated wire may have a circular cross-section shape. It will be understood that other cross-section shapes may be used, such as rectangular, square, triangular, hexagonal, or other geometric shapes.

In the embodiment of the Nitinol alloy substrate, at block 306, a protective layer, such as an electroactive protective layer may applied on the Nitinol alloy. The protective layer may be comprised of nickel or gold. This block is optional based on the material of the substrate.

At block 307, a platinum layer is applied to the alloy wire or the alloy/core wire. In the embodiment of the Nitinol alloy substrate, the protective layer may be between the Nitinol alloy substrate and the platinum layer. In some embodiments, the platinum layer is formed using a DFT process. In this way, the core of the selected alloy and an outer tube of platinum is drawn until the desired thickness is achieved. In some embodiments, the platinum layer can be applied to the alloy or the alloy/core wire using an electroplating process or chemical deposition. The electroplating or deposition processes allow precise control of the thickness of the platinum layer. It is preferable that the platinum be directly layered or deposited on the alloy or alloy/core wire, but in some cases, it may be desirable to have an intervening layer, for example, such as when Nitinol alloy is selected as the substrate and the protective layer is applied. It will be understood that other processes may be used to apply the platinum to the alloy or alloy/core wire.

At block 308, after the platinum has been applied to the substrate, the working wire is processed by applying a biological membrane layer, or multiple biological membrane layers, to provide for the electrochemical processes necessary to operate as a biological sensor. The working wire is then associated with a reference electrode and in some cases, protective coatings may be added to the working wire. As such, this biological sensor may be made for use, for example, with a continuous glucose monitoring device.

Figure 4:
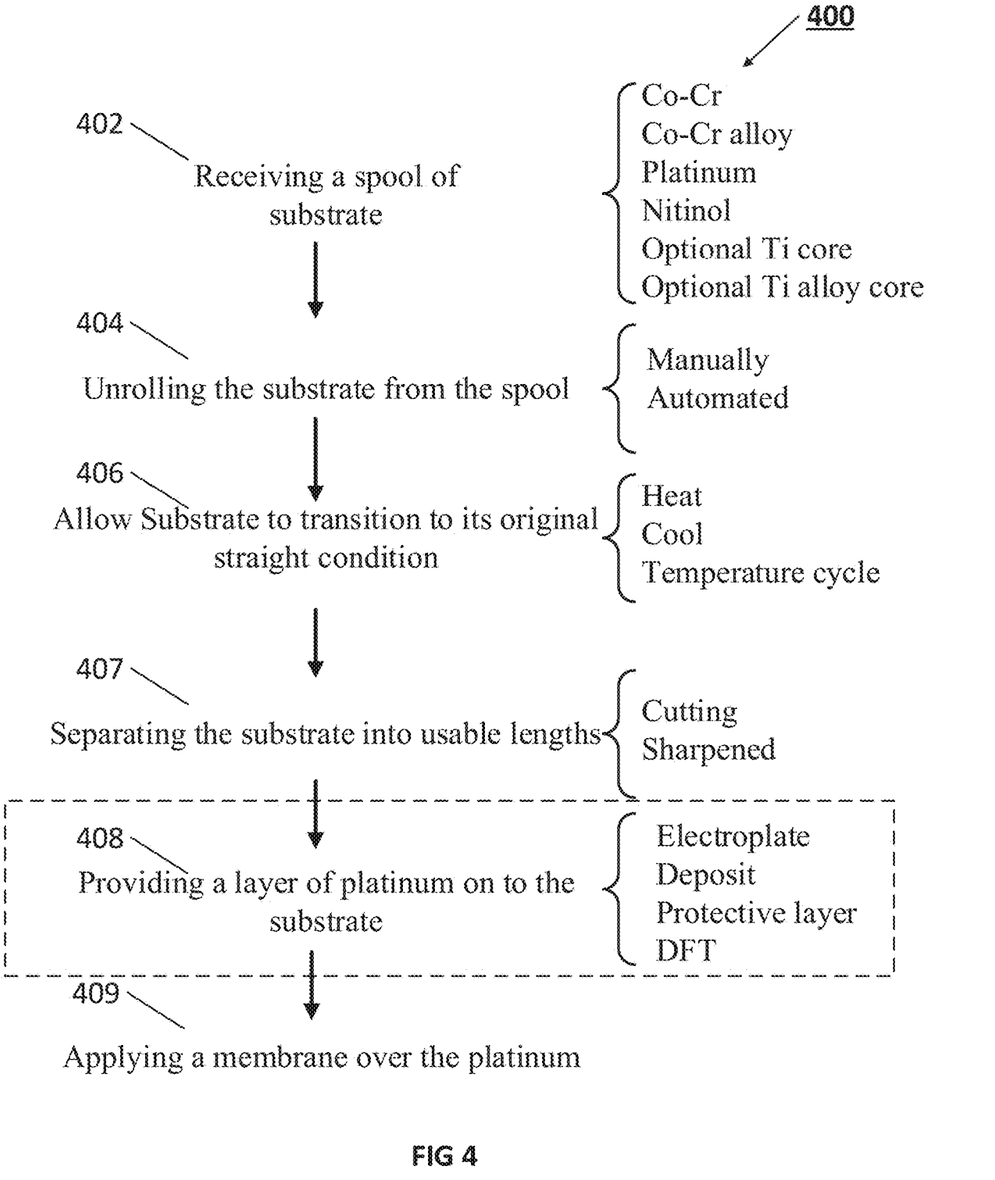

FIG. 4 is a flowchart of a method 400 of manufacturing a working wire for a biological sensor, in accordance with some embodiments. It will be understood that the blocks represent only the primary steps of a manufacturing process, and that one skilled in the art will understand the additional processes and details may be needed to manufacture or produce the working wire. At block 402, the substrate is received in a wound position, such as on a spool, that is to be processed into a working wire. The spool may have a typical arrangement, and be comprised of two disks rotatably supported in coaxial spaced-apart relation to each other, and a hub located between the disks for having the substrate wound thereon.

As described herein, the substrate may be Co—Cr, a Co—Cr alloy, a Co—Cr alloy with a core (alloy/core), Nitinol alloy, or Nitinol alloy with a core (alloy/core). The substrate may be formed in one of several possible cross-sections, such as round, square, rectangular, trapezoidal, oblong, or other geometrical shape. When originally manufactured, the substrate may have been produced in a straight, linear position then heat treated or annealed so that it retains a memory shape. To facilitate ease of distribution and automated manufacturing processes, the substrate may be wound onto spools. It will be appreciated that the spool of substrate may be received without a platinum layer, or the substrate may already have a layer of platinum. In the case of using the Nitinol alloy, a protective layer of gold or nickel, for example, may be set between the Nitinol alloy and the platinum layer.

Once received into the manufacturing facility for the working wire, at block 404, the substrate is unwound or unrolled from the wound position on the spool. This may be a manual process, or an automated process by a machine. At block 406, the substrate is allowed to transition from the wound position to a linear position such that the substrate returns to its original straight shape. This eliminates any circular deformation caused by being in the wound or rolled position on the spool. In some embodiments, the substrate may return to its original straight shape automatically as it is unrolled. In other embodiments, an additional process such as applying a thermal cycle to the substrate may be used to aid or speed the transition of the substrate to the linear position. The thermal cycle may include exposing the substrate to a temperature higher than an ambient temperature, such as heating; exposing the substrate to a temperature lower than the ambient temperature, such as cooling; or moving ambient air around the substrate, such as airflow. In some embodiments, other treatments may be used to aid the transition of the substrate to its original, straight, linear condition.

At block 407, the substrate is separated into lengths suitable for the working wire. The lengths suitable for the working wire may be according to dimensions needed to support the further manufacture of the working wire, which is typically 10 to 40 mm. It will be understood that these usable lengths may be the length of a single working wire, or can be sized to support multiple working wires and may include additional lengths to support the manufacturing process. Further, it will be understood that as the substrate is in a linear position with manageable, suitable lengths, further manufacturing processes, such as dipping and electroplating, may be done more efficiently, accurately and consistently as compared to a substrate which has a bend, curved arc, or other deformation as a result of being in a wound position. Optionally, the tip of one end of the substrate may be shaped or sharpened or made into a pointed formation in order to enable the finished working wire to be inserted under the patient's skin without an inserter needle. It will be understood that this step of sharpening or providing a sharpened point on the substrate may occur at alternative steps of the manufacturing process.

At block 408 a platinum layer is provided on the substrate. The platinum layer comprises platinum. In some embodiments, the platinum layer is formed using a DFT process. In some embodiments, the platinum layer is deposited or electroplated onto the substrate. In some embodiments, the substrate is received in block 402 without a platinum layer and the providing comprises applying the platinum layer on the substrate prior to receiving the substrate in the wound position. Thus, in some embodiments, block 408 is optional after block 407, if the substrate is initially manufactured with the platinum layer. It will be appreciated that the platinum may be applied at other steps in the process, such as before the separating of block 407.

At block 409, a biological membrane is deposited over the platinum layer. It will be understood by one skilled in the art that other layers and materials may be deposited over substrate to form a working wire.

While the specification has been described in detail with respect to specific embodiments of the invention, it will be appreciated that those skilled in the art, upon attaining an understanding of the foregoing, may readily conceive of alterations to, variations of, and equivalents to these embodiments. These and other modifications and variations to the present invention may be practiced by those of ordinary skill in the art, without departing from the scope of the present invention, which is more particularly set forth in the appended claims. Furthermore, those of ordinary skill in the art will appreciate that the foregoing description is by way of example only, and is not intended to limit the invention.

What is claimed is:

1. A working wire for a continuous glucose monitoring sensor, comprising:
   a substrate of the working wire for the continuous glucose monitoring sensor consisting of cobalt-chromium (Co—Cr) alloy, wherein the substrate is produced having an original shape of a straight, linear position, and heat treated or annealed thereby exhibiting a shape memory effect;
   a platinum layer comprising platinum on the substrate; and
   a membrane layer comprising a biological membrane applied over the platinum layer;
   wherein a thickness of the working wire is in a range from 0.0025 inches to 0.005 inches.

2. The working wire of claim 1, wherein the substrate further comprises a core, the core comprising titanium, titanium alloy, Ti-6Al-4V, or vanadium alloy.

3. The working wire of claim 1, wherein the substrate is an elongated wire having a circular cross-section.

4. The working wire of claim 1, wherein:
   a thickness of the platinum layer is in a range from 20 microns to 100 microns.

5. The working wire of claim 1, wherein the platinum of the platinum layer is applied on the substrate by a Drawn Filled Tube (DFT) process.

6. The working wire of claim 1, wherein the platinum of the platinum layer is deposited using chemical deposition or electroplating.

7. The working wire of claim 1, wherein the membrane layer is polyurethane based.

8. The working wire of claim 1, wherein the membrane layer being for continuous glucose monitoring.

9. The working wire of claim 1, wherein a distal end of the working wire is shaped to a pointed formation.

10. The working wire of claim 1, wherein the working wire naturally transitions from a wound position to the original shape of the straight, linear position.

11. The working wire of claim 1, wherein the substrate returns to the original shape of a straight, linear position when a deforming load is released.

\* \* \* \* \*